(12) United States Patent
Kumar

(10) Patent No.: US 8,883,503 B2
(45) Date of Patent: Nov. 11, 2014

(54) HYDROGEL SCAFFOLDS FOR TISSUE ENGINEERING

(75) Inventor: Ashok Kumar, Jammu (IN)

(73) Assignee: Indian Institute of Technology Kanpur, Kanpur (IN)

( * ) Notice: Subject to any disclaimer, the term of this patent is extended or adjusted under 35 U.S.C. 154(b) by 0 days.

(21) Appl. No.: 13/885,839

(22) PCT Filed: Aug. 8, 2011

(86) PCT No.: PCT/IB2011/053521
§ 371 (c)(1),
(2), (4) Date: May 16, 2013

(87) PCT Pub. No.: WO2012/176023
PCT Pub. Date: Dec. 27, 2012

(65) Prior Publication Data
US 2013/0236971 A1    Sep. 12, 2013

(30) Foreign Application Priority Data
Jun. 23, 2011    (IN) .......................... 1774/DEL/2011

(51) Int. Cl.
*C12N 5/00* (2006.01)
*C12N 5/071* (2010.01)
*A61L 27/52* (2006.01)
*A61L 27/38* (2006.01)
*A61L 27/26* (2006.01)

(52) U.S. Cl.
CPC .............. *C12N 5/0602* (2013.01); *A61L 27/52* (2013.01); *A61L 27/38* (2013.01); *A61L 27/26* (2013.01)
USPC ........... 435/395; 428/421; 428/515; 428/516; 428/518; 435/396; 435/397; 525/56; 525/57; 525/209; 525/389

(58) Field of Classification Search
CPC .......... C08L 29/04; C08L 39/06; C08L 57/06
USPC .............. 525/56, 57, 209, 389; 428/421, 515, 428/516, 518; 435/395, 396, 397
See application file for complete search history.

(56) References Cited

U.S. PATENT DOCUMENTS

| 5,104,729 | A | * | 4/1992 | Stedronsky ................. 428/304.4 |
| 5,258,453 | A | | 11/1993 | Kopecek et al. |
| 5,925,012 | A | | 7/1999 | Murphy-Chutorian et al. |
| 5,998,580 | A | | 12/1999 | Fay et al. |
| 6,107,466 | A | | 8/2000 | Hasan et al. |
| 6,281,015 | B1 | | 8/2001 | Mooney et al. |
| 6,337,198 | B1 | | 1/2002 | Levene et al. |
| 6,350,527 | B1 | * | 2/2002 | Hubbell et al. ................ 428/473 |
| 6,524,274 | B1 | | 2/2003 | Rosenthal et al. |
| 6,541,022 | B1 | | 4/2003 | Murphy et al. |
| 6,652,902 | B2 | | 11/2003 | Hubbell et al. |
| 6,748,954 | B2 | | 6/2004 | Lee et al. |
| 6,767,928 | B1 | | 7/2004 | Murphy et al. |
| 6,894,161 | B2 | | 5/2005 | Desjardins et al. |
| 7,186,413 | B2 | | 3/2007 | Bouhadir et al. |
| 7,575,759 | B2 | | 8/2009 | Murphy et al. |
| 2003/0191458 | A1 | | 10/2003 | Diamond et al. |
| 2004/0247527 | A1 | | 12/2004 | Spangler et al. |
| 2008/0166409 | A1 | * | 7/2008 | St. John et al. ............... 424/486 |
| 2011/0059176 | A1 | | 3/2011 | Moro et al. |
| 2013/0295156 | A1 | | 11/2013 | Cottone et al. |

FOREIGN PATENT DOCUMENTS

| WO | WO-96/23543 | 8/1996 |
| WO | WO-2005/056025 | 6/2005 |

OTHER PUBLICATIONS

Hannachi, I.E., et al.; Journal of Internal Medicine, 2009, p. 54-70.*
Kwon, O.H., et al.; Biomaterials, 2003, p. 1223-1232.*
Hirose, M., et al.; Biomacromolecules, 2000, p. 377-381.*
Chapekar, M.S., "Tissue engineering: Challenges and opportunities.," *J. Biomed. Mater. Res.* (Appl. Biomater.) 53, 2000, pp. 617-620.
Chen, Chun-Hung et al., Novel Living Cell Sheet Harvest System Composed of Thermoreversible Methylcellulose Hydrogels, *Biomacromolecules* 2006, 6, pates 736-743.
Da silva, R., et al, "Smart thermoresponsive coatings and surfaces for tissue engineering: switching cell-material boundaries," *Trends. Biotechnol.* 25, 2007, pp. 577-583.
Edelman, et al., "In vitro-cultured meat production." *Tissue Engineering*, vol. 11(5-6), 2005, pp. 659-662.
Ferrier, R.J.,"Carbohydrate boronates," *Adv. Carb. Chem. Biochem.* 35, 1978, pp. 31-80.
Hisamitus, I. et al., Glucose-responsive gel from phenylborate polymer and poly(vinylalcohol): prompt response at physiological pH through the interaction of borate with amino group in the gel. *Pharm Res..* 14, 1997, pp. 289-293.
International Search Report and Written Opinion for PCT/IB2011/053521, mailed Dec. 1, 2011.
Kim et al., Development of Biodegradable and Injectable Macromers Based on Poly(Ethylene Glycol) and Diacid Monomers, *J Biomed Mater Res A*. vol. 90(4), 2009, pp. 1010-1020.
Kitano, S. et al., "A novel drug delivery system utilizing a glucose responsive polymer complex between poly (vinyl alcohol) and poly (n-vinyl-2-pyrrolidone) with a phenylboronic acid moiety." Journal of Controlled Release, 19 (1992) pp. 162-170.
Kitano, S. et al., "Glucose-responsive complex formation between poly(vinyl alcohol) and poly(N-vinyl-2-pyrrolidone) with pendent phenylboronic acid moieties," *Makromol Chem., Rapid. Commun.* 12, 1991, pp. 227-233.
Kitano, S., et al., "Effect of the incorporation of amino groups in a glucose-responsive polymer complex having phenylboronic acid moieties." *Polym. Adv. Technol.* 2, 1992, pp. 261-264.

(Continued)

*Primary Examiner* — Robert Jones, Jr.
(74) *Attorney, Agent, or Firm* — Foley & Lardner LLP

(57) ABSTRACT

Disclosed herein are biodegradable hydrogel scaffolds for use in tissue engineering. The hydrogel scaffolds are composed of synthetic terpolymers complexed with polyvinyl alcohol (PVA), which facilitate cell-sheet and tissue growth. In the presence of a monosaccharide, the PVA-hydrogel is dissolved and cell-sheets are released for harvesting. Further disclosed herein are methods for producing PVA hydrogels which support tissue growth. Tissue engineering applications and methods are also disclosed.

20 Claims, 3 Drawing Sheets

(56) References Cited

OTHER PUBLICATIONS

Langer, R. et al, "Tissue engineering," *Science* 260, 1993, pp. 920-926.

Lu, Pei-Lin et al., "Carbodiimide cross-linked hyaluronic acid hydrogels as cell sheet delivery vehicles: characterization and interaction with corneal endothelial cells," *J. Biomater. Sci. Polymer Edn*, vol. 19, No. 1, pp. 1-18, 2008.

Matsumoto, Akira et al., "Glucose-responsive polymer gel bearing phenylborate derivative as a glucose-sensing moiety operating at the physiological pH," *Biomacromolecules*, 2004 5 (3), pp. 1038-1045.

Qiu, Yong et al., "Environment-sensitive hydrogels for drug delivery," Advance Drug Delivery Reviews 53, (2001), pp. 321-339.

Yamato, M. et al., "Cell sheet engineering," *Materials Today*, (7) 2004, pp. 42-47.

Yang, J. et al., "Cell sheet engineering: Recreating tissues without biodegradable scaffolds," *Biomaterials* 26, 2005, pp. 6415-6422.

Andreopoulos, F.M. et al., "Delivery of Basic Fibroblast Growth Factor 9bFGF) from Photoresponsive Hydrogel Scaffolds," Biomaterials, 2006, vol. 27, pp. 2468-2476.

Chen, R.R. et al., "Polymeric Growth Factor Delivery Strategies for Tissue Engineering," Pharmaceutical Research, Aug. 2003, vol. 20, No. 8, pp. 1103-1112.

Delong, S.A. et al., "Covalently immobilized gradients of bFGF in hydrogel scaffolds for directed cell migration," Biomaterials, 2005, vol. 26, pp. 3227-3234.

Ellis-Davies, G.C.R., "Caged Compounds: photorelease technology for control of cellular chemistry and physiology," Nature Publishing Group, Aug. 2007, vol. 4, No. 8, pp. 619-628.

Frechet, J.M.J. et. al., "Chemically Amplified Imaging Materials based on Acid-Catalyzed Reactions of Polyesters or Electrophilic Croasslinking Processes," Journal of Photopolymer Science and Technology, 1990, vol. 3, No. 3, pp. 235-247.

International Preliminary Report on patentability on PCT/US2010/052817, issued May 1, 2012.

International Search Report and Written Opinion for PCT/US2010/052817 mailed Feb. 3, 2011.

Johnson, J.A. et al., "Synthesis of Photocleavable Linear Macromonomers by ATRP and Star Macromonomers by a Tandem ATRP-Click Reaction: Precursors to Photodegradable Model Networks," American Chemical Society, Mar. 2007, vol. 40, pp. 3589-3598.

Non-Final Office Action on U.S. Appl. No. 13/925,612 dated Dec. 18, 2013.

Notice of Allowance on U.S. Appl. No. 12/605,744, mail date Mar. 30, 2012.

Notice of Allowance on U.S. Appl. No. 12/615,744, mail date Mar. 25, 2013.

Prud'Homme, R. K., et al., "The Effects of Shear History on the Rheology of Hydroxypropyl Guar Gels", in Polymers in Aqueous Media: Performance Through Association, Glass, J.E., Ed., Advances in Chemistry, (1989), vol. 223, pp. 89-112, American Chemican Society.

Richardson, T.P. et al., "Polymeric System for Dual Growth Factor Delivery," Nature Publishing Group, Nov. 2001, vol. 19, pp. 1029-1034.

* cited by examiner

HYDROGEL SCAFFOLDS FOR TISSUE ENGINEERING

CROSS-REFERENCE TO RELATED APPLICATIONS

This application is the U.S. national stage application of International Patent Application No. PCT/IB2011/053521, filed on Aug. 8, 2011, which claims priority to Indian Patent Application No. 01774/DEL/2011, filed on Jun. 23, 2011. The aforementioned applications are incorporated herein by reference in their entirety.

TECHNICAL FIELD

The present disclosure relates generally to tissue engineering and scaffold matrices therefor. In particular, the present disclosure includes biocompatible hydrogels for cell-sheet and tissue production.

BACKGROUND

The following description is provided to assist the understanding of the reader. None of the information provided or references cited is admitted to be prior art.

Biological scaffolds are natural or artificial structures capable of facilitating a variety of physiological processes. Such scaffolds can be formed in situ or in vitro as prefabricated matrices defined by a specific shape or structure. These scaffolds serve multiple purposes, such as, supporting cell or tissue attachment, migration, delivery, and retention. In addition to cells and/or tissues, biological scaffolds can contain bioactive agents, pharmaceutical compounds, and/or fluids, e.g., cell growth medium. As such, biological scaffolds can be seeded with cells and cultured in vitro or directly implanted into a tissue. However, three-dimensional tissue engineering requires additional considerations relating to scaffold-tissue matrices.

Tissue engineering involves the use of biological macromolecules and living cells to develop suitable substitutes for tissue or organ replacement. In order for such complex structures to develop, however, the biological scaffolds from which they form must support cell and tissue growth that is similar to natural tissue organogenesis. Along these lines, tissue engineering applications require structures composed of varying degrees of thickness and size, which can affect tissue durability. The structure and stability of newly formed tissues can vary and, for applications requiring scaffold removal, a non-disruptive separation of the scaffold-tissue complex is necessary to ensure the integrity of the tissue. Accordingly, mechanisms for severing the scaffold-tissue complex constitutes an important consideration in the development of new strategies for tissue engineering.

SUMMARY

In one aspect, the present disclosure provides a hydrogel scaffold composition including one or more polyvinyl alcohol polymers and one or more phenylboronate-containing copolymers. In illustrative embodiments, the one or more phenylboronate-containing copolymers are composed of one or more phenylboronate ligands, one or more acrylic monomers, and one or more alkaline tertiary amines. In illustrative embodiments, the one or more phenylboronate ligands are selected from 4-vinylphenylboronic acid, N-acryloyl-3-aminophenylboronic acid, 3-(2-carboxyvinyl)phenylboronic acid, 4-(1,6-dioxo-2,5-diaza-7-oxamyl)phenylboronic acid, and [2-(diethylamino)carbonyl-4-bromomethyl]phenylboronate, or any combination thereof.

In illustrative embodiments, the one or more acrylic monomers are selected from acrylamide; N-isopropylacrylamide; N,N-dimethylacrylamide; 2-hydroxyethylmethacrylate; N-Hydroxyethyl acrylamide; methacrylamide; methacrylic acid; acrylic acid; N-vinyl-2-pyrrolidone; 4-pentenoic acid; N-isopropylmethacrylamide; N-methoxymethyl-N-isopropylacrylamide; and 2-(dimethylmaleimido)-N-ethylacrylamide, or any combination thereof. In illustrative embodiments, the one or more alkaline tertiary amines are selected from N,N-dimethylaminoethylmethacrylate; N,N-dimethylaminopropylacrylamide; N,N-diethylaminoethyl methacrylate; and 2-(N,N-Dimethylamino)ethyl methacrylate, or any combination thereof.

In illustrative embodiments, the hydrogel scaffold is biodegradable. In illustrative embodiments, the hydrogel scaffold is susceptible to degradation by saccharides. In illustrative embodiments, the saccharides are monosaccharides. In illustrative embodiments, the saccharides are selected from fructose, glucose, mannitol, L-arabinose, D-xylose, D-galactose, D-mannose, L-fucose, N-acetyl-D-galactosamine, N-acetyl-D-glucosamine, and N-acetylneuraminic acid, or any combination thereof, or any combination thereof.

In one aspect, the present disclosure provides a method for producing a hydrogel scaffold, which includes mixing one or more polyvinyl alcohol polymers with one or more phenylboronate-containing copolymers to form a mixture and allowing the mixture to congeal. In illustrative embodiments, the one or more phenylboronate-containing copolymers are composed of one or more phenylboronate ligands, one or more acrylic monomers, and one or more alkaline tertiary amines. In illustrative embodiments, the methods include dissolving the one or more polyvinyl alcohol polymers prior to mixing the one or more polyvinyl alcohol polymers with the one or more phenylboronate-containing copolymers.

In illustrative embodiments, dissolving the one or more polyvinyl alcohol polymers prior to mixing the one or more polyvinyl alcohol polymers with the one or more phenylboronate-containing copolymers occurs at a temperature of at least 70° C. In illustrative embodiments, the one or more polyvinyl alcohol polymers are cooled to at least 40° C. after dissolving the one or more polyvinyl alcohol polymers and prior to mixing the one or more polyvinyl alcohol polymers with the one or more phenylboronate-containing copolymers. In illustrative embodiments, mixing the one or more polyvinyl alcohol polymers with the one or more phenylboronate-containing copolymers to form the mixture occurs at a pH from 5 to 9. In illustrative embodiments, the mixture is allowed to congeal for 2-8 hours. In illustrative embodiments, the hydrogel scaffold is produced in the absence of copolymer grafting.

In one aspect, the present disclosure provides a method for tissue engineering, which includes culturing cells on a hydrogel scaffold including one or more phenylboronate-containing copolymers to form one or more cell-layers, dissolving the hydrogel scaffold with a saccharide solution, and harvesting the one or more cell-layers. In illustrative embodiments, the hydrogel scaffold is composed of one or more polyvinyl alcohol polymers. In illustrative embodiments, the one or more phenylboronate-containing copolymers are composed of one or more phenylboronate ligands, one or more acrylic monomers, and one or more alkaline tertiary amines.

In illustrative embodiments, the one or more phenylboronate ligands are selected from 4-vinylphenylboronic acid, N-acryloyl-3-aminophenylboronic acid, 3-(2-carboxyvinyl) phenylboronic acid, 4-(1,6-dioxo-2,5-diaza-7-oxamyl)phenylboronic acid, and [2-(diethylamino)carbonyl-4-bromomethyl]phenylboronate, or any combination thereof. In illustrative embodiments, the one or more acrylic monomers are selected from acrylamide; N-isopropylacrylamide; N,N-dimethylacrylamide; 2-hydroxyethylmethacrylate; N-Hydroxyethyl acrylamide; methacrylamide; methacrylic acid; acrylic acid; N-vinyl-2-pyrrolidone; 4-pentenoic acid; N-isopropylmethacrylamide; N-methoxymethyl-N-isopropylacrylamide; and 2-(dimethylmaleimido)-N-ethylacrylamide, or any combination thereof.

In illustrative embodiments, the one or more alkaline tertiary amines are selected from N,N-dimethylaminoethylmethacrylate; N,N-dimethylaminopropylacrylamide; N,N-diethylaminoethyl methacrylate; and 2-(N,N-Dimethylamino)ethyl methacrylate, or any combination thereof. In illustrative embodiments, culturing the cells on the hydrogel scaffold occurs at a pH from 5 to 9. In illustrative embodiments, the cells are cultured for 5-20 days. In illustrative embodiments, the cells are selected from keratinocytes, fibroblasts, hepatocytes, glial cells, endothelial cells, epidermal cells, limbal stem cells, periodontal stem cells, bone marrow stromal cells, stem cells, mammalian cells, bacterial cells, insect cells, human cells, skin cells, muscle cells, epithelial cells, umbilical vessel cells, corneal cells, cardiomyocytes, aortic cells, corneal epithelial cells, aortic endothelial cells, hair cells, melanocytes, adipose cells, bone cells, osteoblasts, airway cells, microvascular cells, mammary cells, vascular cells, chondrocytes, and placental cells, or any combination thereof.

In illustrative embodiments, the cells are grown to confluence. In illustrative embodiments, the saccharide solution is a monosaccharide solution. In illustrative embodiments, the saccharide solution is selected from a fructose solution, glucose solution, mannitol solution, L-arabinose solution, D-xylose solution, D-galactose solution, D-mannose solution, L-fucose solution, N-acetyl-D-galactosamine solution, N-acetyl-D-glucosamine solution, and N-acetylneuraminic acid solution, or any combination thereof. In illustrative embodiments, dissolving the hydrogel scaffold with a saccharide solution occurs in the absence of proteolytic enzymes. In illustrative embodiments, the cell-layers are transferred to a cell-support membrane.

In illustrative embodiments, the cell-support membrane is hydrophilic PVDF. In illustrative embodiments, the one or more cell-layers are suitable for cell and tissue grafting, skin-grafting, allografting, wound healing grafts, skin replacement, ocular reconstruction, liver tissue reconstruction, cardiac patching, bladder augmentation, ligament cell sheet patching, bone tissue repair and reconstruction, thyroid tissue reconstruction, esophageal ulcer patching, and tracheal reconstruction, or any combination thereof. In illustrative embodiments, the one or more cell-layers represent a monolayer. In illustrative embodiments, the one or more cell-layers are stratified layers. In illustrative embodiments, the stratified layers are different cell-types. In illustrative embodiments, the stratified layers form spheroid cell-bodies, tubular cell-bodies, hollow cell-bodies, graded porosity masses, or solid masses, or any combination thereof.

In one aspect, the present disclosure provides a kit for tissue engineering including one or more polyvinyl alcohol polymers, one or more phenylboronate-containing copolymers, one or more saccharide solutions, and instructions for the tissue engineering. In illustrative embodiments, the one or more phenylboronate-containing copolymers include one or more phenylboronate ligands, one or more acrylic monomers, and one or more alkaline tertiary amines. In illustrative embodiments, the one or more phenylboronate ligands are selected from 4-vinylphenylboronic acid, N-acryloyl-3-aminophenylboronic acid, 3-(2-carboxyvinyl)phenylboronic acid, 4-(1,6-dioxo-2,5-diaza-7-oxamyl)phenylboronic acid, and [2-(diethylamino)carbonyl-4-bromomethyl]phenylboronate, or any combination thereof.

In illustrative embodiments, the one or more acrylic monomers are selected from acrylamide, N-isopropylacrylamide, N,N-dimethylacrylamide; 2-hydroxyethylmethacrylate; N-Hydroxyethyl acrylamide; methacrylamide; methacrylic acid; acrylic acid; N-vinyl-2-pyrrolidone; 4-pentenoic acid; N-isopropylmethacrylamide; N-methoxymethyl-N-isopropylacrylamide; and 2-(dimethylmaleimido)-N-ethylacrylamide, or any combination thereof. In illustrative embodiments, the one or more alkaline tertiary amines are selected from N,N-dimethylaminoethylmethacrylate; N,N-dimethylaminopropylacrylamide; N,N-diethylaminoethyl methacrylate; and 2-(N,N-dimethylamino)ethyl methacrylate, or any combination thereof.

In illustrative embodiments, the one or more saccharide solutions are monosaccharide solutions. In illustrative embodiments, the one or more saccharide solutions is selected from a fructose solution, glucose solution, mannitol solution, L-arabinose solution, D-xylose solution, D-galactose solution, D-mannose solution, L-fucose solution, N-acetyl-D-galactosamine solution, N-acetyl-D-glucosamine solution, and N-acetylneuraminic acid solution, or any combination thereof.

The foregoing summary is illustrative only and is not intended to be in any way limiting. In addition to the illustrative aspects, embodiments, and features described above, further aspects, embodiments, and features will become apparent by reference to the following drawings and the detailed description.

BRIEF DESCRIPTION OF THE FIGURES

FIGS. 2A-2E show fibroblasts cultured on poly-(DMAAm-VPBA-DMAEMA)-PVA hydrogels at days 2, 6, 8, 10, and 12, respectively. FIG. 2F depicts fibroblasts grown on poly-(AAm-VPBA-DMAEMA)-PVA after 12 days in culture. FIG. 2G shows fibroblasts grown on poly-(NIPAAm-VPBA-DMAEMA)-PVA after 12 days in culture. FIGS. 2H-2L show fibroblasts grown on poly-(AAm-VPBA-DMAEMA)-PVA after 15 days in culture, which have detached as cell-sheet monolayers after fructose treatment.

FIGS. 3A-3C show keratinocytes grown to confluence on poly-(AAm-VPBA-DMAEMA)-PVA hydrogels at day 6. FIGS. 3D-3K show confluent keratinocytes after fructose treatment, which have detached as cell-sheet monolayers.

DETAILED DESCRIPTION

Figure 1:
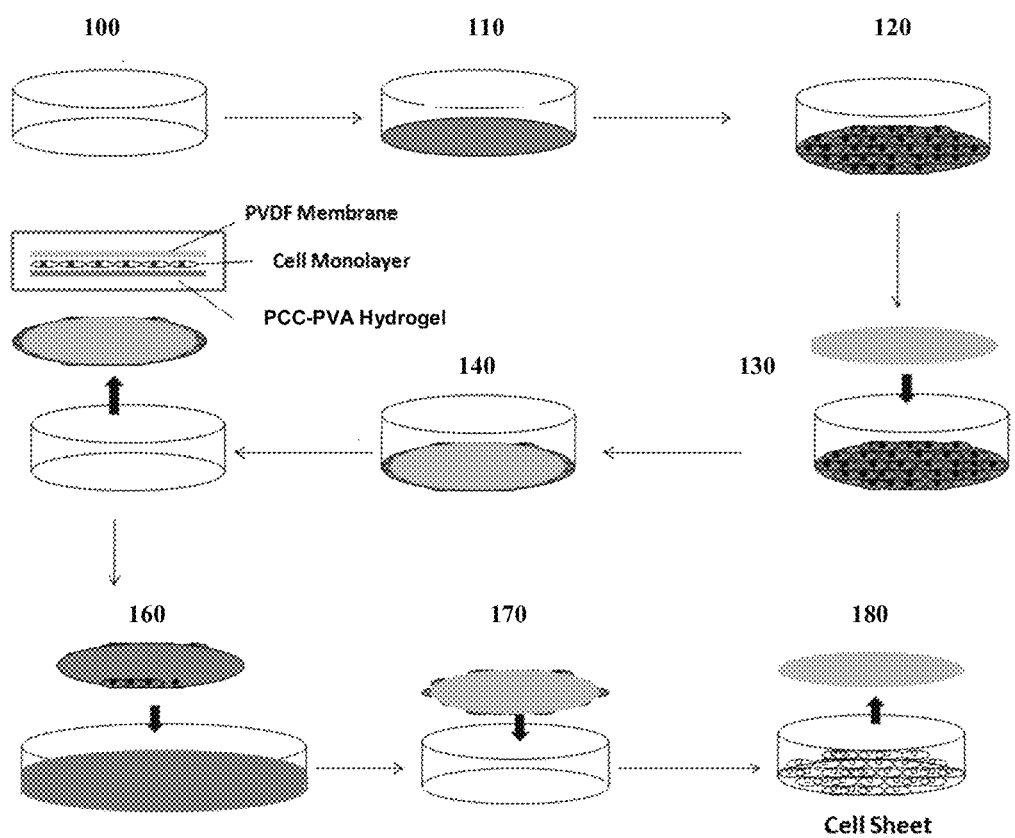
FIG. 1 is an illustrative embodiment of a flow diagram of a method for hydrogel-based tissue engineering.

In the following detailed description, reference is made to the accompanying drawings, which form a part thereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

As used herein, unless otherwise stated, the singular forms "a," "an," and "the" include plural reference. Thus, for example, a reference to "a tissue" can include a plurality of tissues.

As used herein, the term "about" will be understood by persons of ordinary skill in the art and will vary to some extent depending upon the context in which it is used. If there are uses of the term which are not clear to persons of ordinary skill in the art, given the context in which it is used, the term "about" in reference to quantitative values will mean up to plus or minus 10% of the enumerated value.

As used herein, the term "biocompatible polymer" refers to a synthetic or natural material that is, for example, non-toxic to biological systems and/or congruent with biological processes. In this respect, biocompatibility of polymer materials denote minimal, negligible, or no risk of immunorejection, injury, damage and/or toxicity to living cells, tissues, organs, and/or biological systems. In illustrative embodiments, the biocompatible polymer is also biodegradable and/or susceptible to saccharide degradation. In illustrative embodiments, the biocompatible polymer is, for example, but not limited to, polyvinyl alcohol (PVA), polylactic acid (PLA), polyglycolic acid (PGA), poly(lactide-co-glycolide) (PLGA) and/or poly (L-lactide) (PLLA), and the like.

As used herein, the term "biodegradable" or "biodegradation" refers generally to the decomposition, i.e., breaking down, of materials, such as, for example, biological or natural material, organic matter, biocompatible materials, biocompatible polymers, and/or biosynthetic materials, when exposed to a biodegradative agent. In illustrative embodiments, "biodegradation" includes, but, is not limited to, biolytic degradation, proteolytic degradation, lipolytic degradation, saccharide degradation, degradation by microorganisms, such as, e.g., bacteria, fungi, viruses, and the like, and degradation by other natural or synthetic processes that are compatible with one or more biological systems or environments.

As used herein, the term "carbohydrates" will be understood by one skilled in the art to include polyhydroxy-aldehydes or -ketones and compounds derived therefrom. Carbohydrates can include compounds composed of at least one basic monosaccharide unit. They may be classified as simple carbohydrates and/or complex carbohydrates. Simple carbohydrates are monosaccharides and disaccharides. Complex carbohydrates are polysaccharides, or large molecules composed of straight or branched chains of monosaccharides. "Monosaccharides", as defined herein, typically have the general formula $C_x(H_2O)_y$ and contain either a ketone or aldehyde functional group. Monosaccharides also typically contain a hydroxyl groups on non-carbonyl carbon atoms. Non-limiting examples of monosaccharides include erythrose, threose, arabinose, ribose, xylose, glucose, mannose, galactose, fructose and/or sorbose.

As used herein, the terms "extracellular matrix" or "ECM," are used interchangeably, and encompass various liquid, gelatinous, semi-solid, or solid protein mixtures congruent with the complex extracellular environment found in many tissues. The extracellular matrix may be employed as a substrate for cell and tissue culture preparations or as a surface for cell adhesion to a hydrogel matrix. The "extracellular matrix" may also include basement membrane extract and/or Engelbreth-Holm-Swarm (EHS) matrix. In illustrative embodiments, Matrigel™ (BD Biosciences, Franklin Lakes, N.J.) is employed as the EMC, when necessary for particular applications.

As used herein, the terms "hydrogel" or "hydrogel matrix" are used interchangeably, and encompass polymer and non-polymer based hydrogels. "Hydrogel" is also meant to refer to all other hydrogel compositions disclosed herein, including hydrogels that contain polymers, copolymers, terpolymer, and complexed polymer hydrogels, i.e., hydrogels that contain one, two, three, four or more monomeric or multimeric constituent units. Along the same lines, the terms "tissue hydrogel" or "tissue matrix" refer to any composition formed into a porous matrix into which cells or tissue can grow in three dimensions. Hydrogels are typically continuous networks of hydrophilic polymers that absorb water.

As used herein, the term "organ" refers to a part or structure of the body, which is adapted for a special function or functions, and includes, but is not limited to, the skin, the lungs, the liver, the kidneys, and the bowel, including the stomach and intestines. In particular, it is contemplated that organs which are particularly susceptible to dysfunction and failure arising from an injury are amendable to tissue-engineered reconstruction and are encompassed by the term "organ."

As used herein, the term "polymer" refers to a macromolecule made of repeating monomer or multimer units. Polymers of the present disclosure, include, but are not limited to, poly(hyaluronic acid), poly(sodium alginate), poly(ethylene glycol) (PEG), poly(lactic acid) polymers, poly(glycolic acid) polymers, poly(lactide-co-glycolides) (PLGA), poly (urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly (vinyl alcohol) (PVA), poly(acrylic acid), poly(vinyl acetate), polyacrylamide, poly(ethylene-co-vinyl acetate), poly(methacrylic acid), polylactic acid (PLA), poly(L-lactide) (PLLA), polyglycolic acids (PGA), nylons, polyamides, polyanhydrides, poly(ethylene-co-vinyl alcohol) (EVOH), polycaprolactone, polyvinylhydroxide, poly(ethylene oxide) (PEO), and polyorthoesters or a co-polymer or terpolymer formed from at least two or three members of the groups, respectively. The terms "hydrogel polymers" or "matrix polymer materials" refer to the materials used to make the hydrogels of the present disclosure. The terms refer to both monomeric units of the materials and the polymers or co-polymers made therefrom. Individual matrix units (monomers) or polymers can be biocompatible, biodegradable, saccharide biodegradable and/or non-biodegradable.

As used herein, the terms "saccharide degradation" or "saccharide biodegradation" or "saccharide biodegradable" refer to the decomposition, i.e., breaking down, of materials such as, for example, biocompatible polymers, co-polymers, terpolymers, and the like, when exposed to a saccharide solution. In illustrative embodiments, biocompatible polymers are susceptible to saccharide degradation by, for example, saccharide catalyzed displacement, competitive binding of saccharides, and/or sequestration of polymer units via saccharide interaction, and the like. In illustrative embodiments, the saccharides are monosaccharides, disaccharides, oligosaccharides, or polysaccharides, and the like, that bind polymers such as, for example, phenylboronate-containing copolymers (PCCs), with increased affinity compared to other PCC-polymer intermolecular interactions, e.g., PVA-PCC. The rate of degradation may be fast, e.g., degradation may take place in minutes, or slow, e.g., degradation may take place over hours, days, weeks or months, or the polymer may degrade in response to a particular saccharide concentration.

In illustrative embodiments, the rate of degradation can be controlled by the type of saccharide and/or polymer that is used.

As used herein, the terms "scaffolding polymers" or "scaffolding materials" refer to the materials used to generate hydrogel scaffolds. The terms refer to both monomeric units of the materials and the polymers made therefrom. Individual scaffolding units (monomers) or polymers can be biocompatible, biodegradable, saccharide biodegradable, and/or non biodegradable.

As used herein, the term "tissue" or "tissues" refer to singular or multiply-layered structures, e.g., monolayers or stratified layers of cells, which typically constitute organ constituents. One or more different tissues may form an organ or organs. An organ may also be composed of only one type of tissue or cell. In illustrative embodiments, "tissue," for example, emanates from one or more various types of cell layers. In this regard, tissues are composed of, for example, one or more cell-types, which include, but are not limited to, cells, muscle cells, epithelial cells, endothelia cells, stem cells, umbilical vessel cells, corneal cells, cardiomyocytes, aortic cells, corneal epithelial cells, aortic endothelial cells, fibroblasts, hair cells, keratinocytes, melanocytes, adipose cells, bone cells, osteoblasts, airway cells, microvascular cells, mammary cells, vascular cells, chondrocytes, and/or placental cells, and the like.

Tissue Engineering Scaffolds

Hydrogel matrices can be used as conformable, malleable, or injectable conduits for in situ or in vivo administration of cells, drugs, or tissues to a subject. Hydrogels also function as scaffolds that facilitate in vitro and ex vivo cell growth, thereby allowing for cell-sheet and/or tissue formation prior to, or simultaneous with, administration to a subject. Synthetic hydrogels can be sterilized and do not have the associated risk of harboring contaminants, e.g., infectious agents. However, synthetic hydrogels typically do not mimic the extracellular matrix (ECM) and therefore may not properly direct cellular ingrowth or function. Hydrogels composed of a ECM imitate the native cellular environment. However, unless such hydrogels are made from autologous material, i.e., recognized as "self" by the immune system, immunorejection is possible.

Moreover, removal of the supporting matrix on which the cells or tissue constructs grow may be required for complete tissue reconstruction. Separation of the hydrogel matrix from tissue that has formed therewith typically disrupts ECM and cellular junctions of the tissue. Accordingly, tissue engineering is enhanced by the manufacture of biodegradable scaffolds that allow for in vitro, ex vivo, in vivo, or in situ confluent cell growth, such that cells, cell-sheets, and/or tissue constructs can be harvested in a non-invasive manner, e.g., by saccharide biodegradation and/or without the use of proteolytic enzymes. In this respect, the present disclosure advantageously provides hydrogel scaffolds, wherein cells, cell-sheets, and/or tissues are grown and harvested as contiguous cell-layers with intact cell-cell junctions and deposited ECM.

The harvested cells, cell-sheets, and/or tissues can be applied to various cell or tissue reconstruction applications, including, but not limited to, cell and tissue grafting, skin-grafting, allografting, wound healing grafts, aesthetic or functional re-modeling grafts, skin replacement, ocular reconstruction, liver tissue reconstruction, cardiac patching, bladder augmentation, ligament cell sheet patching, bone tissue repair and reconstruction, cartilage tissue repair and reconstruction, vasculature repair and reconstruction, thyroid tissue reconstruction, esophageal ulcer patching, neuronal tissue repair, pancreatic tissue repair, and tracheal reconstruction. Furthermore, in vitro cell culturing supports cell adhesion, cell viability, and cell proliferation on the hydrogel scaffolds disclosed herein, which, for example, demonstrates their general biocompatibility.

The biocompatibility of the hydrogel scaffolds emanate at least partially from the mild synthesis procedures described herein, which do not involve the use of harsh chemicals and/or gelation techniques. In addition, the hydrogel scaffolds possess monosaccharide inducible gel-sol phase transformability. As such, the hydrogel scaffolds are suitable for cell-sheet and tissue engineering, as well as cell immobilized applications relating thereto. The hydrogel scaffolds can be applied for immobilizing various types of mammalian cells, including but not limited to, hybridoma cells, kidney cells, Chinese hamster ovaries (CHO) cells, pancreatic islets, corneal epithelial cells, fibroblasts, chondrocytes, articular chondrocytes, neuroblasts, vascular endothelial cells, hepatocytes, esophageal epithelial cells, and erythrocytes. The immobilization can be achieved through various procedures, including but not limited to, adhesion, matrix entrapment, and microencapsulation. Hydrogels are typically composed of various monomeric constituents, and polymers, copolymers, or terpolymers thereof.

Polymer hydrogels are suitable matrix materials because they can be readily manufactured with a wide range of reproducible properties and structures. Depending on their composition, polymer matrices provide varying degrees of mechanical support for withstanding compressive and/or tensile forces. In this regard, maintaining the shape and integrity of the matrix can be important for certain tissue engineering applications, such as implanting newly formed tissue or a tissue-matrix complex into a subject. Typical tissue-matrix structures include various types of polymer hydrogels, which differ in their susceptibility to biodegradation.

The morphology of a hydrogel scaffold may also influence the development of tissue structure. The size, shape, and vascularization of various tissues, moreover, impart their functional characteristics within a biological system. Accordingly, it is important to properly design hydrogel scaffolds to facilitate a suitable range of mechanical and biological functions. Synthetic polymeric materials can be precisely controlled in material properties, quality, and mode of manufacture. Further, the present disclosure enables the production of synthetic polymers by various techniques, thereby providing for a consistent supply of such hydrogels in large quantities. The mechanical and physical properties of synthetic polymers can be readily adjusted through variation of molecular structures so as to fulfill their functions without the use of either fillers or additives.

A variety of polymers can be utilized to fabricate hydrogel matrices for cell-sheet and tissue production. These materials are typically employed as structural elements in the hydrogel, and include, but are not limited to, poly(hyaluronic acid), poly(sodium alginate), poly(ethylene glycol) (PEG), poly(lactic acid) polymers, poly(glycolic acid) polymers, poly(lactide-co-glycolides) (PLGA), poly(urethanes), poly(siloxanes) or silicones, poly(ethylene), poly(vinyl pyrrolidone), poly(2-hydroxy ethyl methacrylate), poly(N-vinyl pyrrolidone), poly(methyl methacrylate), poly(vinyl alcohol) (PVA), poly(acrylic acid), poly(vinyl acetate), polyacrylamide, poly(ethylene-co-vinyl acetate), poly(methacrylic acid), polylactic acid (PLA), poly(L-lactide) (PLLA), polyglycolic acids (PGA), nylons, polyamides, polyanhydrides, poly(ethylene-co-vinyl alcohol) (EVOH), polycaprolactone, polyvinylhydroxide, poly(ethylene oxide) (PEO). Some of these polymers are extensively used in biomedical applications such as drug delivery and are FDA approved for a variety of applications. A number of biocompatible polymers, such as, e.g., PVA, PGA, PLA, PLLA, PLGA, and other synthetic polymer tissue matrices are also known in the art. In illustrative embodiments, the hydrogel matrix is composed of PVA.

Polymers and copolymers of PVA are odorless, water-absorbing structures with a wide range of physical properties that can mimic conventional polymers. When exposed to moisture or biological fluids, the properties of PVA can vary depending upon the type of fluid and concentration thereof. Along these lines, water reduces the tensile strength of PVA by acting as a plasticiser, but, conversely, increases its elongation and tear durability. Accordingly, PVA polymers and copolymers can form stable, biocompatible hydrogels with controlled biodegradation, e.g., via saccharide biodegradation as detailed below.

In one aspect, the present disclosure provides a PVA-based hydrogel for tissue engineering. PVA is a resilient polymer that can be dissolved in an appropriate solvent. PVA is also hydrophilic and amenable to crosslinking. Hence, the use of PVA as a scaffolding constituent provides a suitable, biodegradable component for hydrogel production and tissue engineering. In illustrative embodiments, the concentration of PVA in a PVA-based hydrogel is from about 0.1, 0.5, 1, 1.5, 2, 2.5, 3, 3.5, 4, 5, 10, 20, or 30% (w/v) to from about 0.25, 0.5, 1, 1.5, 2, 2.5, 3, 3.5, 4, 5, 10, 20, or 30% (w/v). In illustrative embodiments, the concentration of PVA in a PVA-based hydrogel is from about 2% to about 3% (w/v). In illustrative embodiments, the concentration of PVA in a PVA-based hydrogel is at least about 2.5% (w/v).

The foregoing PVA hydrogel complexes are durable, yet biodegradable, when complexed with phenylboronate-containing copolymers (PCCs). Structures containing PVA are capable of binding PCCs, which imparts a PCC-PVA hydrogel complex that is capable of facilitating cell and/or tissue growth. In illustrative embodiments, the PCCs of the present disclosure contain one or more phenylboronate ligands, acrylic monomers, and alkaline tertiary amines. Accordingly, prior to PCC-PVA hydrogel formation, the PCC constituents are reacted together to produce the resulting PCC terpolymer.

The phenylboronate ligands of the present disclosure are derivatized forms of phenylboronic acid (PBA). Such PBA derivatives confer biocompatibility and biodegradative properties, e.g., saccharide biodegradation, to the PCC terpolymers, in illustrative embodiments. To this end, PBA forms specific and reversible covalent interactions with 1,2- or 1,3-cis-diol-containing compounds such as, but not limited to, carbohydrates, glycoproteins, nucleosides, nucleotides, nucleic acids, catechols, and/or various other molecules or enzymes. Accordingly, phenylboronates are useful for synthesizing biodegradable hydrogel matrices, which can be dissolved in a saccharide solution. In illustrative embodiments, the phenylboronate ligands include, but are not limited to, 3-(2-carboxyvinyl)phenylboronic acid, 4-(1,6-dioxo-2,5-diaza-7-oxamyl)phenylboronic acid, [2-(diethylamino)carbonyl-4-bromomethyl]phenylboronate, catechol [2-(diisopropylamino) carbonyl]phenylboronate, catechol [2-(diethylamino)carbonyl, 4-methyl]phenylboronate, p-bromophenylboronate, p-(waminoethyl)phenylboronate, p-vinylbenzeneboronate, N-acryloyl-m-aminophenylboronic acid (NAAPBA), 4-vinylphenylboronic acid (VPBA) and/or N-acryloyl-3-aminophenylboronic acid (AAPBA). In illustrative embodiments, the phenylboronate ligand includes VPBA. In illustrative embodiments, the phenylboronate ligand includes AAPBA.

In illustrative embodiments, the phenylboronate ligand is added in an amount from about 0.001, 0.01, 0.1, 0.2, 0.3, 0.4, or 0.5% (w/v) to from about 0.01, 0.1, 0.2, 0.4, 0.6, 0.8, 1, 1.5, 2, 2.5, 3, 3.5, 4, 5, 10 or 20% (w/v). In illustrative embodiments, the phenylboronate ligand is added in an amount from about 0.5% (w/v) to from about 1% (w/v). In some embodiments, VPBA is added in an amount from about 0.001, 0.01, 0.1, 0.2, 0.3, 0.4, or 0.5% (w/v) to from about 0.01, 0.1, 0.2, 0.4, 0.6, 0.8, 1, 1.5, 2, 2.5, 3, 3.5, 4, 5, 10 or 20% (w/v). In illustrative embodiments, VPBA is added in an amount from about 0.5% (w/v) to from about 1% (w/v). In suitable embodiments, AAPBA is added in an amount from about 0.001, 0.01, 0.1, 0.2, 0.3, 0.4, or 0.5% (w/v) to from about 0.01, 0.1, 0.2, 0.4, 0.6, 0.8, 1, 1.5, 2, 2.5, 3, 3.5, 4, 5, 10 or 20% (w/v). In illustrative embodiments, AAPBA is added in an amount from about 0.5% (w/v) to from about 1% (w/v).

In addition to the phenylboronate ligands, PCCs are also composed of acrylic monomers, which are polymerized with the phenylboronate ligands in the presence of an initiator molecule. Such acrylic monomers include, but are not limited to, 2-hydroxyethylmethacrylate; N-hydroxyethyl acrylamide; methacrylamide; methacrylic acid; acrylic acid; N-vinyl-2-pyrrolidone; 4-pentenoic acid; N-isopropylmethacrylamide; N-methoxymethyl-N-isopropylacrylamide; 2-(dimethylmaleimido)-N-ethylacrylamide; methacrylate; ethylacrylate; n-butyl acrylate (NBA), hydroxyethylmethacrylate, methylmethacrylate, acrylamide (AAm), N-isopropylacrylamide (NIPAAm), and/or N,N-dimethylacrylamide (DMAAm). These acrylic monomers are known in the art and can be adapted for various uses as required. In illustrative embodiments, the acrylic monomers can be one or more of AAm, NIPAAm, and DMAAm.

In illustrative embodiments, the acrylic monomer is added in an amount from about 0.01, 0.1, 1, 2, 3, 4, 5, 6, 7, or 8% (w/v) to from about 0.1, 1, 2, 3, 4, 5, 6, 7, 8, 9, 10, 20 or 30% (w/v). In some embodiments, the acrylic monomer is added in an amount from about 8% (w/v) to from about 9% (w/v). In suitable embodiments, AAm is added in an amount from about 0.01, 0.1, 1, 2, 3, 4, 5, 6, 7, or 8% (w/v) to from about 0.1, 1, 2, 3, 4, 5, 6, 7, 8, 9, 10, 20 or 30% (w/v). In illustrative embodiments, AAm is added in an amount from about 8% (w/v) to from about 9% (w/v). In illustrative embodiments, NIPAAm is added in an amount from about 0.01, 0.1, 1, 2, 3, 4, 5, 6, 7, or 8% (w/v) to from about 0.1, 1, 2, 3, 4, 5, 6, 7, 8, 9, 10, 20 or 30% (w/v). In some embodiments, NIPAAm is added in an amount from about 8% (w/v) to from about 9% (w/v). In illustrative embodiments, DMAAm is added in an amount from about 0.01, 0.1, 1, 2, 3, 4, 5, 6, 7, or 8% (w/v) to from about 0.1, 1, 2, 3, 4, 5, 6, 7, 8, 9, 10, 20 or 30% (w/v). In illustrative embodiments, DMAAm is added in an amount from about 8% (w/v) to from about 9% (w/v). Acrylic monomer concentrations are added in appropriate amounts, such that the properties of the resulting copolymer and/or terpolymer are not altered in response thereto. The skilled artisan will readily recognize that various concentrations and combinations of the foregoing acrylic monomers can be applied for a desired use.

In illustrative embodiments, the PCC-PVA hydrogels of the present disclosure are biodegradable via saccharide degradation. Scaffolds derived from acrylic monomers and/or polyethylene glycol (PEG), however, are typically non-biodegradable. Even so, such polymers have been extensively studied as hydrogel constituents. See, e.g., Kim et al., *Development of Biodegradable and Injectable Macromers Based on Poly(Ethylene Glycol) and Diacid Monomers, J Biomed Mater Res A*. Vol. 90(4): 1010-1020 (2009). One reason for employing such incompatible monomers is that they provide the lattice or matrix network within a hydrogel complex; and even though these monomers are typically non-degradable, they can be employed as precursor constituents to biodegradable matrices, via saccharide degradation, in the presence of suitable initiator molecules, i.e., tertiary amines.

Alkaline tertiary amines are compounds, such as trimethylamine, that include three organic moieties covalently bound to a nitrogen, under alkaline conditions. The pH of biochemical reactions occurring in the presence of suitable concentrations of such tertiary amines functions to facilitate biological interactions, e.g., at a desired pH range. In illustrative embodiments, the pH ranges from about 1, 2, 3, 4, 5, 6, 7 or 8 to from about 5, 6, 7, 8, 9, 10, 11, 12, 13 or 14. In some embodiments, the pH ranges from about 5, 6, 7 or 8 to from about 6, 7, 8 or 9. In illustrative embodiments, the pH is about 7 or 7.4, i.e., physiological pH. In illustrative embodiments, the incorporation of tertiary amine groups into the hydrogel polymer backbone increases polymer hydrophilicity and swelling. Moreover, many compounds that incorporate alkaline tertiary amines are soluble in acidic media via protonation of the amine groups. In illustrative embodiments, the alkaline tertiary amine promotes the formation of the PCC-PVA complex.

In this regard, the amine-assisted PCC-PVA interactions of the present disclosure enable the production of hydrogel scaffolds capable of sustaining cell and tissue growth. Alkaline tertiary amines such as, but not limited to, e.g., N,N-dimethylaminoethyl methacrylate (DMAEMA); N,N-dimethylaminopropyl acrylamide; N,N-diethylaminoethyl methacrylate; 2-(diethylamino) ethyl methacrylate (DEAEMA); 2-(N,N-dimethylamino)ethyl methacrylate; 2-(N-morpholino) ethyl methacrylate (MEMA); and 2-(diisopropylamino) ethyl methacrylate (DPAEMA) are employed to stabilize the PCC-PVA interactions. In illustrative embodiments, DMAEMA is the alkaline tertiary amine employed for facilitating the formation of PCC-PVA hydrogels at physiological pH.

In illustrative embodiments, an alkaline tertiary amine is added in an amount from about 0.001, 0.01, 0.1, 0.2, 0.3, 0.4, or 0.5% (w/v) to from about 0.01, 0.1, 0.2, 0.4, 0.6, 0.8, 1, 1.5, 2, 2.5, 3, 3.5, 4, 5, 10 or 20% (w/v). In suitable embodiments, an alkaline tertiary amine is added in an amount from about 0.5% (w/v) to from about 1% (w/v). In illustrative embodiments, DMAEMA is added in an amount from about 0.001, 0.01, 0.1, 0.2, 0.3, 0.4, or 0.5% (w/v) to from about 0.01, 0.1, 0.2, 0.4, 0.6, 0.8, 1, 1.5, 2, 2.5, 3, 3.5, 4, 5, 10 or 20% (w/v). In illustrative embodiments, DMAEMA is added in an amount from about 0.5% (w/v) to from about 1% (w/v).

Thus, in the presence of an alkaline tertiary amine, the PCC-PVA interactions are stable at physiological pH. As such, in the presence of appropriate competitive binding agents, such as, for example, saccharides, biodegradation can be readily achieved. In illustrative embodiments, an alkaline tertiary amine is incorporated into the PCC terpolymer structure, thereby allowing for the PCC-PVA co-polymer to form at a desired pH, which stabilizes the phenylboronate-diol complex at a suitable pH, e.g., physiological pH.

In one aspect, the hydrogel scaffold is susceptible to degradation by saccharide displacement, which can be achieved, for example, via competitive binding. In illustrative embodiments, the saccharides are monosaccharides that bind PCCs with increased affinity compared to PVA-PCC intermolecular interactions. In this way, PVA-PCC hydrogels degrade or dissolve when, in the presence of at least one monosaccharide, the monosaccharide displaces, i.e., competes off, PCC-bound PVA. Advantageously, saccharide degradation of the PVA-PCC hydrogel is non-disruptive to the cells, cell-sheets, and/or tissues cultured therewith. In illustrative embodiments, the monosaccharides include, but are not limited to, erythrose, threose, arabinose, ribose, xylose, glucose, mannose, galactose, fructose, sorbose, mannitol, fucose, N-acetyl-D-galactosamine, N-acetyl-D-glucosamine, or N-acetylneuraminic acid, or any combination thereof. In illustrative embodiments the monosaccharides are monosaccharide solutions containing one or more monosaccharides.

The configuration of the foregoing saccharide residues, for example, as furanoside or as pyranoside, are both applicable as degradative solvents. In illustrative embodiments, the saccharide configurations can predominantly exist in, for example, pyranose form, furanose form, or both in solution. In illustrative embodiments, the monosaccharide capable of degrading or dissolving the PCC-PVA hydrogel is fructose. In some embodiments, the monosaccharide capable of degrading or dissolving PCC-PVA hydrogel is glucose. In illustrative embodiments, both fructose and glucose are employed separately, sequentially, or simultaneously as biodegradative agents.

In illustrative embodiments, the concentration of fructose required for hydrogel biodegradation is from about 10, 50, 100, 150, 200, 250, or 300 mM to from about 100, 150, 200, 250, 300, 350, 400, 500, 700, 900, or 1000 mM. In some embodiments, the concentration of fructose required for hydrogel biodegradation is from about 150 mM to from about 250 mM. In illustrative embodiments, the concentration of fructose required for hydrogel biodegradation is at least about 200 mM. Similarly, the concentration of glucose required for hydrogel biodegradation is from about 10, 50, 100, 150, 200, 250, or 300 mM to from about 100, 150, 200, 250, 300, 350, 400, 500, 700, 900, or 1000 mM. In illustrative embodiments, the concentration of glucose required for hydrogel biodegradation is from about 150 mM to from about 250 mM. In illustrative embodiments, the concentration of glucose required for hydrogel biodegradation is at least about 200 mM.

Methods for Hydrogel Scaffold Production and Tissue Engineering

In one aspect, the present disclosure provides PCC terpolymer complexes composed of three constituent units, including one or more phenylboronate ligands, one or more acrylic monomers, and one or more alkaline tertiary amines. As such, a variety of PCCs can be produced by varying the constituent polymers. These PCC terpolymers include, but are not limited to, NIPAAM-co-VPBA-co-DMAEMA (NVD terpolymer), AAm-co-VPBA-co-DMAEMA (AVD terpolymer), and DMAAm-co-VPBA-co-DMAEMA (DVD terpolymer). In illustrative embodiments, the PCC terpolymer is complexed with PVA to form a PCC-PVA hydrogel. In illustrative embodiments, the PCC-PVA hydrogel is a NVD, AVD, and/or, DVD terpolymer complexed with PVA.

Such PCC terpolymers are complexed with PVA to produce a biocompatible and biodegradable, e.g., via saccharide biodegradation, hydrogel as disclosed herein. Methods for producing such hydrogel scaffolds include mixing one or more PVA polymers with one or more PCCs to form a co-polymer mixture, wherein the mixture is subsequently allowed to congeal. In this regard, illustrative embodiments of the present disclosure provide for a PVA solution which dissolves in a liquid to a final concentration from about 0.1, 0.5, 1, 1.5, 2, 2.5, 3, 3.5, 4, 5, 10, 20, or 30% (w/v) to from about 0.25, 0.5, 1, 1.5, 2, 2.5, 3, 3.5, 4, 5, 10, 20, or 30% (w/v). In illustrative embodiments, PVA is dissolved in a liquid to a final concentration from about 1, 1.5 or 2% (w/v), to from about 2.5 or 3.0% (w/v). In illustrative embodiments, PVA is dissolved in a liquid solution to a final concentration of about 2.5% (w/v).

Dissolving PVA into solution can be performed by various methods known in the art. It will be readily apparent to the skilled artisan that heating a solution to about 60, 70, 80, 90, 100, 110, 120, or 130° C., or higher temperatures, for about 5-60 minutes (min) will, thereby, dissolve the PVA. In illustrative embodiments, the dissolving is by increasing the temperature to about 80, 90, or 100° C. for about 5-60 min. In some embodiments, the dissolving is by heating, at about 90° C. for about 5-60 min. In illustrative embodiments, the dissolving is by heating for about 30 min. In illustrative embodiments, after dissolving the PVA into solution, the solution is subsequently cooled to room temperature.

In order to produce the PCC-PVA hydrogel complex, equal amounts of the PVA solution and one or more of the PCC terpolymers, e.g., NVD, AVD, and DVD, are added together optionally in tissue culture plate wells and mixed. The mixing can occur at a pH from about 1-14, 2-12, 3-11, 4-10, 5-9, or from about 6-8. In a illustrative embodiments, the mixing occurs at a pH from about 7-8. In illustrative embodiments, the mixing occurs at a physiological or neutral pH.

The hydrogel must properly congeal in order to facilitate a suitable environment for tissue construction. In illustrative embodiments, the hydrogel is allowed to congeal for about 0.5, 1, 2, 3, 4, 5, 6, 7, 8, 9, 10, 20, 30, or 50 hours (h). In some embodiments, the hydrogel is allowed to congeal for about 5, 6, or 7 h. It will be readily apparent to the skilled artisan that numerous additional variables can effect hydrogel polymerization, solidification, or congealing. Such factors include, for example, humidity, $CO_2$ concentration, and/or temperature, etc. The skilled artisan will readily appreciate that appropriate adjustments can optimize cell and tissue production for specific or desired uses. In illustrative embodiments, the hydrogel scaffold is produced in the absence of copolymer grafting.

In one aspect, the present disclosure provides methods for culturing cells on a PCC-PVA hydrogel, thereby forming one or more cell-layers. Subsequently, the hydrogel scaffold is biodegraded or dissolved with an appropriate saccharide solution, e.g., a monosaccharide solution. In illustrative embodiments, one or more cell-layers, cells, tissues, and/or other biological outgrowths are harvested after the hydrogel is dissolved.

The cultured cells are maintained or grown for about 1, 2, 3, 4, 5, 6, 7, 8, 9, 10, 11, 12, 13, 14, 15, 16, 17, 18, 19, 20, 25, 30, 35, 40, or 50 days. In illustrative embodiments, the cells are cultured for about 13, 14, 15, 16, 17, or 18 days. In some embodiments, the cells are cultured until a desired cell density is attained. Cells can also be cultured until they are grown to confluence. The amount of time required for cell culturing may depend upon the type of cell cultured. The skilled artisan will readily appreciate that adjusting or maintaining cell culturing conditions, as needed, provides for robust cell proliferation. Cell culture media, e.g., DMEM, may be maintained and/or replenished as required for suitable cell growth and related tissue engineering applications.

One of skill in the art will be able to determine a suitable growth medium for initial preparation of cells. Commonly used growth media for cell culturing includes, but is not limited to, e.g., Iscove's modified Dulbecco's Media (IMDM) media, DMEM, KO-DMEM, DMEM/F12, RPMI 1640 medium, McCoy's 5A medium, minimum essential medium alpha medium (α-MEM), F-12K nutrient mixture medium (Kaighn's modification, F-12K), X-vivo™ 20, Stemline, CC100, H2000, Stemspan™, MCDB 131 Medium, Basal Media Eagle (BME), Glasgow Minimum Essential Media, Modified Eagle Medium (MEM), Opti-MEM® I Reduced Serum Media, Waymouth's MB 752/1 Media, Williams Media E, Medium NCTC-109, neuroplasma medium, BGJb Medium (Fitton-Jackson Modification), Brinster's BMOC-3 Medium, CMRL Medium, $CO_2$-Independent Medium, Leibovitz's L-15 Media, and the like.

Tissue engineering, moreover, includes producing tissues that emanate from one or more various cell-types. In this respect, the cell-types of the present disclosure include, but are not limited to, e.g., human or mammal skin cells, muscle cells, epithelial cells, endothelia cells, stem cells, umbilical vessel cells, corneal cells, cardiomyocytes, aortic cells, corneal epithelial cells, aortic endothelial cells, fibroblasts, hair cells, keratinocytes, melanocytes, adipose cells, bone cells, osteoblasts, airway cells, microvascular cells, mammary cells, vascular cells, chondrocytes, and placental cells. In illustrative embodiments, fibroblasts are employed for tissue generation. In some embodiments, keratinocytes are employed for tissue generation.

In illustrative embodiments, the one or more cell-layers, include, but are not limited to, cell-layers that are suitable for cell and tissue grafting, skin-grafting, allografting, wound healing grafts, skin replacement, ocular reconstruction, liver tissue reconstruction, cardiac patching, bladder augmentation, ligament cell sheet patching, bone tissue repair and reconstruction, thyroid tissue reconstruction, esophageal ulcer patching, and tracheal reconstruction, or any combination thereof. Moreover, the one or more cell-layers, cells, tissues, and/or other biological outgrowths include, but are not limited to, monolayers, stratified layers, spheroid cell-bodies, tubular cell-bodies, hollow cell-bodies, graded porosity masses, or solid masses, or any combination thereof.

Wound healing applications include the use of purified or isolated cells for repairing or regenerating tissue or differentiated cell lineages in a subject. Such methods include, for example, procuring stem cells or differentiated cells from a subject in need of tissue repair or regeneration. The cells are cultured in accord with the methods described herein, e.g., with PCC-PVA hydrogels for a desired time or until a desired cell density is attained. In illustrative embodiments, the hydrogels are subsequently biodegraded, for example, using a saccharide solution, and the resulting cells, cell-sheets, and/or tissues are administered to a subject (e.g., a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, and genetic disorders or similar diseases), where an increase or replacement of a particular cell type/tissue is desirable.

In illustrative embodiments, the intact hydrogel with regenerated cells, cell-sheets, and/or tissues is administered to a subject (e.g., a subject having a myocardial infarction, congestive heart failure, stroke, ischemia, peripheral vascular disease, alcoholic liver disease, cirrhosis, Parkinson's disease, Alzheimer's disease, diabetes, cancer, arthritis, wound healing, immunodeficiency, aplastic anemia, anemia, and genetic disorders or similar diseases). In this respect, the hydrogel-cell complex is directly implanted into the subject. Such tissue engineering applications decrease handling of cells and the hydrogel, ex vivo, prior to implantation. Accordingly, potential cell or tissue damage is reduced or eliminated. Once implanted, the hydrogels are dissolved in the host, e.g., via biodegradation from circulating bodily saccharides.

In some embodiments, the subject has damage to a tissue or organ, and administering the regenerated cells, cell-sheets, and/or tissues provides for a sufficient increase in biological function of the tissue or organ or to increase the number of cells present in the tissue or organ. In illustrative embodiments, the subject has a disease, disorder, or condition, and wherein the administering provides a dose of cells sufficient to ameliorate or stabilize the disease, disorder, or condition. In yet another embodiment, the subject has a deficiency of a particular cell type, such as a circulating blood cell type and wherein the administering restores such circulating blood cells.

Furthermore, cell and tissue applications can be implemented in accord with the present methods to increase production of commodity goods. In this regard, synthetic or in vitro cultured meat, for example, allows for the low cost generation of foodstuffs. See, e.g., Edelman, et al., "In vitro-cultured meat production." Tissue Engineering, Vol. 11(5-6), pp. 659-662 (2005). In illustrative embodiments, selected animal cells, e.g., muscle or liver cells from animals such as fish, cattle, sheep, turkeys, and the like, are cultured using, inter alia, PCC-PVA hydrogels as described herein. Stem cells, moreover, also afford tissue engineering applications a range of progenitor cells, which can be induced to differentiate into a desired cell type, for the generation of a variety of synthetic meats and the like.

Regardless of any particular hydrogel-based application, e.g., tissue regeneration, synthetic food production, and the like, PCC-PVA hydrogel scaffolds can be dissolved in the presence of one or more monosaccharide solutions in accord with the saccharide biodegradation techniques as disclosed herein. In this respect, the present disclosure provides for harvesting hydrogel-separated cells, cell-sheets, and/or tissue, or any combination thereof. In illustrative embodiments, the monosaccharides are one or more of erythrose, threose, arabinose, ribose, xylose, glucose, mannose, galactose, fructose, sorbose, mannitol, fucose, N-acetyl-D-galactosamine, N-acetyl-D-glucosamine, or N-acetylneuraminic acid, or any combination thereof. In some embodiments, the monosaccharide that dissolves the hydrogel is fructose and/or glucose. In illustrative embodiments, the monosaccharides are monosaccharide solutions containing one or more monosaccharides. Synthetic saccharides can also be employed as described herein. For example, synthetic saccharides, such as enantiomers of naturally occurring monosaccharides can be used for the competitive displacement of PVA from PCC-PVA polymeric structures.

In illustrative embodiments, the concentration of fructose required for hydrogel biodegradation is from about 10, 50, 100, 150, 200, 250, or 300 mM to from about 100, 150, 200, 250, 300, 350, 400, 500, 700, 900, or 1000 mM. In some embodiments, the concentration of fructose required for hydrogel biodegradation is from about 150 mM to from about 250 mM. In illustrative embodiments, the concentration of fructose required for hydrogel biodegradation is at least about 200 mM. It will be readily apparent to the skilled artisan that various temperatures, lengths of time, and other factors will effect the overall degradation of the PCC-PVA hydrogel disclosed herein.

Likewise, the concentration of glucose required to dissolve the PCC-PVA hydrogel, thereby producing the cell and/or tissue product, is from about 10, 50, 100, 150, 200, 250, or 300 mM to from about 100, 150, 200, 250, 300, 350, 400, 500, 700, 900, or 1000 mM. In some embodiments, the concentration of glucose required to dissolve the PCC-PVA hydrogel, thereby producing the cell and/or tissue product, is from about 150 mM to from about 250 mM. In illustrative embodiments, the concentration of glucose required for hydrogel degradation is at least about 200 mM. In this regard, the PCC-PVA hydrogel can be advantageously dissolved in the absence of proteolytic enzymes.

FIG. 1 shows an illustrative embodiment of a method for obtaining a sheet of cells separated from a hydrogel used for cell proliferation. In an operation 100, a tissue plate provides a cell-sheet enclosure. In an operation 110, PCC combines with PVA thereby forming a biodegradable hydrogel. In an operation 120, cells proliferate to a confluent monolayer. In an operation 130, a hydrophilic polyvinylidene fluoride (PVDF) membrane provides cell monolayer support. In an operation 140, the PVDF membrane contacts the cell monolayer via capillary interaction, thereby adhering to the apical surface of the cell monolayer. The PVDF membrane is hydrophilically modified, thereby facilitating the simultaneous binding with the underlying hydrogel. In an operation 150, the PVDF membrane and the hydrogel are separated from the tissue plate and subsequently inverted.

In an operation 160, fructose dissolves the inverted hydrogel-cell monolayer-PVDF membrane complex. In an operation 170, a polystyrene (TCPS) dish accepts the cell monolayer-PVDF membrane complex from which the hydrogel was dissolved. The cell monolayer interacts with the TCPS dish via its basal surface. In an operation 180, a 15-20 min incubation in the presence of DMEM separates the PVDF membrane from the cell-monolayer, thus producing an intact cell-sheet.

Kits and Other Agents Added to Polymers and Tissue Scaffolds

One aspect of the present technology discloses a kit containing reagents and instructions for performing the present disclosure. In illustrative embodiments, a kit for tissue engineering includes one or more polyvinyl alcohol polymers, e.g., PVA, one or more PCCs, one or more saccharide solutions, and instructions for the tissue engineering. In other embodiments, the kit includes one or more phenylboronate ligands, one or more acrylic monomers, and one or more alkaline tertiary amines. In illustrative embodiments, the kit includes either or both of VPBA and AAPBA.

One or more alkaline tertiary amines, such as, but not limited to DMAEMA, may also be included in the kit. In illustrative embodiments, the kit includes one or more acrylic monomers, such as, but not limited to, AAm, NIPAAm, and DMAAm. The kit may also include one or more monosaccharide solutions, such as a fructose or glucose solution. In illustrative embodiments, the kit discloses reagents and instructions for performing or producing any of the methods, steps, procedures or embodiments described herein.

EXAMPLES

The present compositions and methods will be understood more readily by reference to the following examples, which are provided by way of illustration and are not intended to be limiting in any way.

Example 1

Terpolymer Hydrogel Preparation

PVA Hydrogels.

Under sterile conditions, PVA was heated for 30 min at 90° C. in 10 ml of double distilled water to a final concentration of 2.5% (w/v). The solution was then allowed to cool to room temperature. Subsequently, in equal volumes, 100 µl of sterilized PVA solution and one or more of the NVD-(NIPAAM-co-VPBA-co-DMAEMA), AVD-(AAm-co-VPBA-co-DMAEMA), and DVD-(DMAAm-co-VPBA-co- DMAEMA) terpolymer solutions were added to tissue culture plate wells, mixed, and allowed to congeal for 6 hours.

Example 2

Hydrogel Culturing and Recovery of Fibroblasts

NIH3T3 Fibroblasts.

FIG. 1 shows the general procedure for growth, maintenance, and harvesting of cells in Example 2. In 1 ml of Dulbecco's Modified Eagle's Medium (DMEM), $4 \times 10^4$ cells/ml of NIH3T3 fibroblasts were incubated with a hydrogel solution in the tissue culture plate wells for 30 min at 4° C. The cell-hydrogel mixture was then sustained at 37° C. with 5% $CO_2$, and new DMEM was provided every 2-3 days. After 15 days in culture, the DMEM was replaced with 1.5 ml of sterile fructose solution (200 mM) and the tissue culture plates were agitated for 40-45 min at 60 rpm using a vortex shaker (spinix, Torsons) to recover the resulting tissue and cells.

Figure 2:
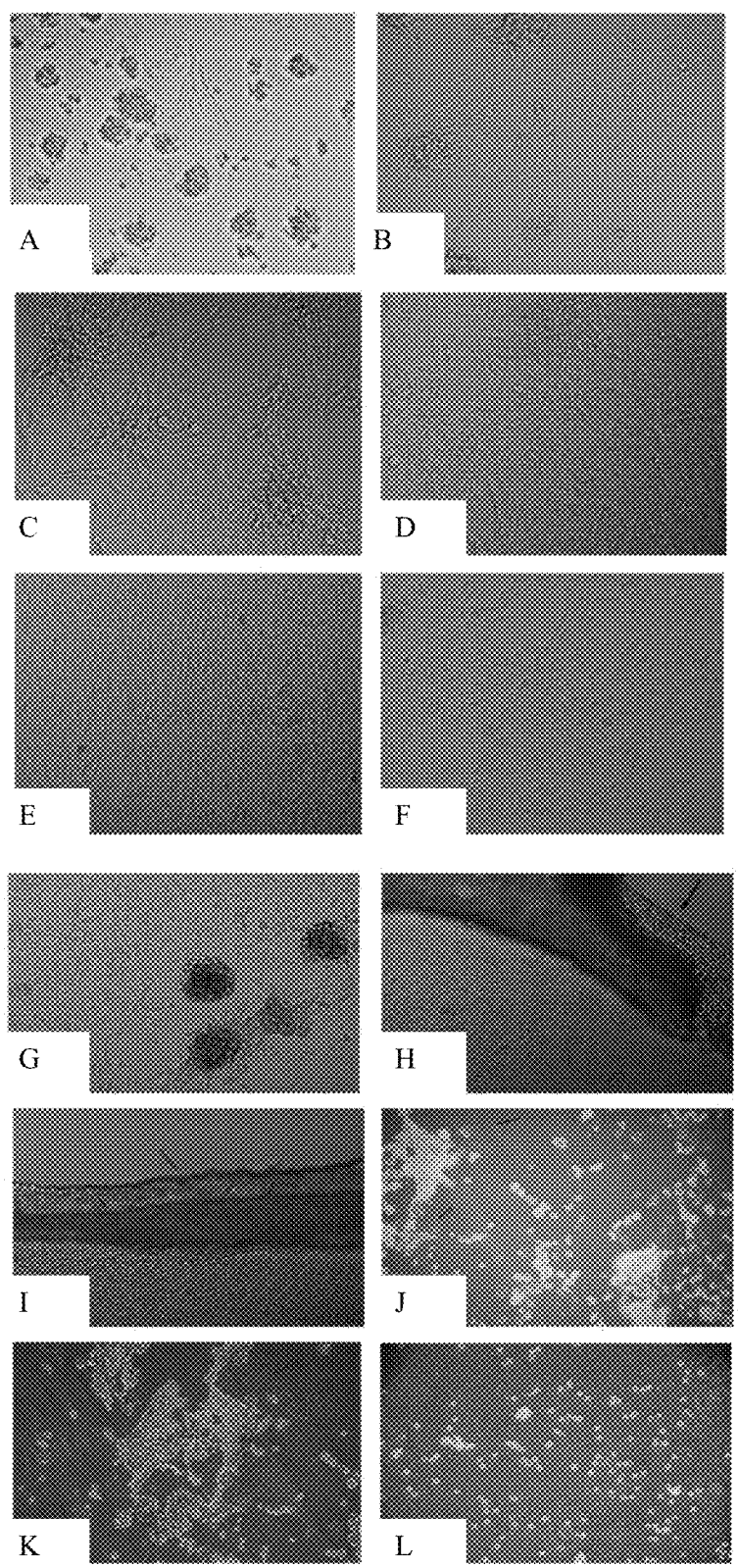
FIGS. 2A-2L show the growth of NIH3T3 fibroblasts at various time points in an illustrative embodiment.

FIGS. 2A-2E show NIH3T3 fibroblasts cultured on poly-(DMAAm-VPBA-DMAEMA)-PVA, i.e., DVD-PVA, hydrogels at days 2, 6, 8, 10, and 12, respectively. As shown in FIG. 2A, cell migration was observed after 24 hours and aggregates formed on the hydrogel. The aggregates demonstrated that the cells remained viable with a round morphology. After 6-8 days in culture, cells began to proliferate as demonstrated by increased fibroblast growth proximal to the aggregates and surrounding hydrogel (FIGS. 2B-2D). By day 12, fibroblast proliferation was robust (FIG. 2E). As shown in FIG. 2F, similar to using a DVD-PVA matrix, when an AVD-PVA hydrogel was employed, the cells attained confluence. However, the NVD-PVA hydrogels did not support the same level of cell proliferation (see FIG. 2G).

FIGS. 2H-2J show confluent NIH3T3 fibroblasts cultured on poly-(AAm-VPBA-DMAEMA)-PVA, i.e., AVD-PVA, hydrogels after 15 days in culture. Following 15 days in culture, cells were harvested by dissolving the AVD-PVA hydrogel by fructose (200 mM) treatment (FIGS. 2H-2J). Cell culture medium was replaced with 1.5 ml of sterilized 200 mM fructose-150 mM sodium chloride (NaCl) and stirred for 20 min at 60 rpm. As shown in FIGS. 2H-2I, the fructose treatment degraded the hydrogel and released a fibroblast monolayer. FIGS. 2J-2L show that continuing fructose treatment resulted in the recovery of cell aggregates (hydrogel remnants are indicated by arrows).

Example 3

Hydrogel Culturing and Recovery of Keratinocytes

HaCat Human Keratinocytes.

Figure 3:
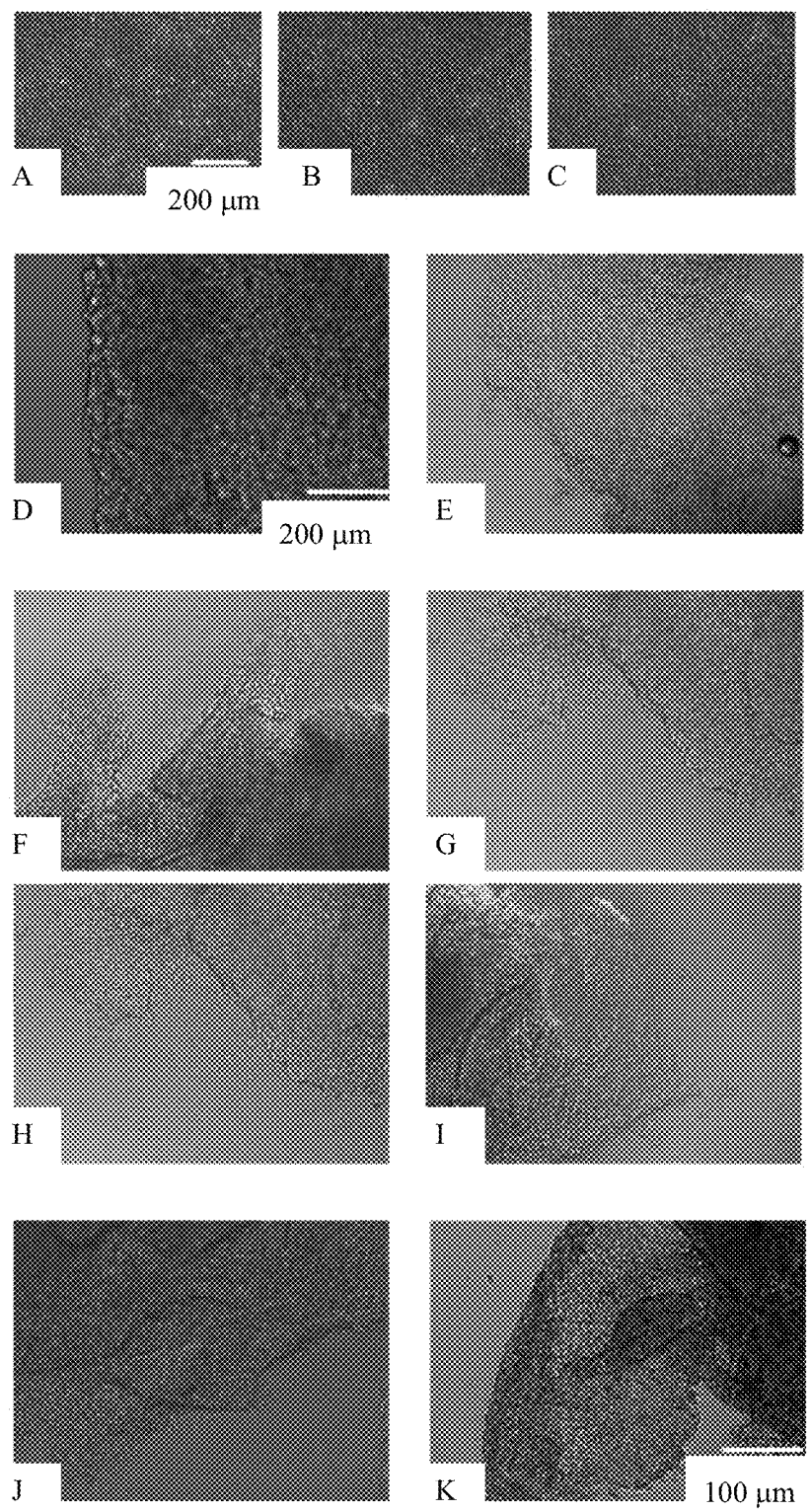
FIGS. 3A-3K show the growth of HaCat human keratinocytes in an illustrative embodiment.

FIG. 1 shows the general procedure for growth, maintenance, and harvesting of cells for Example 3. In 1 ml of DMEM, $4 \times 10^4$ cells/ml of HaCat human keratinocytes were incubated with a AVD-PVA hydrogel solution in the tissue culture plate wells for 30 min at 4° C. The cell-hydrogel mixture was then sustained at 37° C. with 5% $CO_2$, and new DMEM was provided every 2-3 days (FIGS. 3A-3C). Cells were grown to confluence by day 6, and subsequently, DMEM was removed from the wells and cultures were washed with 1.5 ml of phosphate buffer saline (PBS). A hydrophilically modified PVDF membrane (0.45 μm, Millipore, India) was placed in the culture plates and the PBS was aspirated, thereby adhering to the membrane the apical surface of the keratinocytes.

DMEM (200 μl) was added on to the membrane to prevent drying. The cultures were then incubated for 15 min at 37° C. Subsequently, the PVDF membrane, with the attached cell-hydrogel matrix was transferred to a Petri dish containing 10 ml of a 200 mM fructose solution (FIGS. 3D-3K). After degradation of the hydrogel, the membrane-attached keratinocytes were transferred to a treated polystyrene (TCPS) surface. An additional 200 μl of DMEM was added for 15-20 min and the PVDF membrane was removed (FIG. 1).

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 proteins refers to groups having 1, 2, or 3 proteins. Similarly, a group having 1-5 proteins refers to groups having 1, 2, 3, 4, or 5 proteins, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

All references cited herein are incorporated by reference herein in their entireties and for all purposes to the same extent as if each individual publication, patent, or patent application was specifically and individually incorporated by reference in its entirety for all purposes.

The invention claimed is:

1. A hydrogel scaffold composition comprising:
   a hydrogel layer, the hydrogel layer comprising one or more polyvinyl alcohol polymers and one or more phenylboronate-containing copolymers, wherein the hydrogel layer is configured for cell growth into one or more of cell-sheets or tissues; and
   a polyvinylidene fluoride membrane, wherein the polyvinylidene fluoride membrane overlays the hydrogel layer.

2. The composition of claim 1, wherein the one more phenylboronate-containing copolymers includes one or more phenylboronate ligands, one or more acrylic monomers, and one or more alkaline tertiary amines.

3. The composition of claim 2, wherein the one or more phenylboronate ligands are selected from the group consisting of 4-vinylphenylboronic acid, N-acryloyl-3-aminophenylboronic acid, 3-(2-carboxyvinyl)phenylboronic acid, 4-(1,6-dioxo-2,5-diaza-7-oxamyl)phenylboronic acid, and [2-(diethylamino)carbonyl-4-bromomethyl]phenylboronate, or any combination thereof.

4. The composition of claim 2, wherein the one or more acrylic monomers are selected from the group consisting of acrylamide; N-isopropylacrylamide; N,N-dimethylacrylamide; 2-hydroxyethylmethacrylate; N-Hydroxyethyl acrylamide; methacrylamide; methacrylic acid; acrylic acid; N-vinyl-2-pyrrolidone; 4-pentenoic acid; N-isopropylmethacrylamide; N-methoxymethyl-N-isopropylacrylamide; and 2-(dimethylmaleimido)-N-ethylacrylamide, or any combination thereof.

5. The composition of claim 2, wherein the one or more alkaline tertiary amines are selected from the group consisting of N,N-dimethylaminoethylmethacrylate; N,N-dimethylaminopropylacrylamide; N,N-diethylaminoethyl methacrylate; and 2-(N,N-Dimethylamino)ethyl methacrylate, or any combination thereof.

6. The composition of claim 1, wherein the hydrogel scaffold is susceptible to degradation by saccharides.

7. The composition of claim 6, wherein the saccharides are selected from the group consisting of fructose, glucose, mannitol, L-arabinose, D-xylose, D-galactose, D-mannose, L-fucose, N-acetyl-D-galactosamine, N-acetyl-D-glucosamine, and N-acetylneuraminic acid, or any combination thereof.

8. A method for producing the hydrogel scaffold of claim 1 comprising:
   mixing one or more polyvinyl alcohol polymers with one or more phenylboronate-containing copolymers to form a mixture; and
   allowing the mixture to congeal, wherein the scaffold is configured for cell growth into one or more of cell-sheets or tissues.

9. The method of claim 8, wherein the one or more phenylboronate-containing copolymers includes one or more phenylboronate ligands, one or more acrylic monomers, and one or more alkaline tertiary amines.

10. The method of claim 8, further comprising dissolving the one or more polyvinyl alcohol polymers prior to mixing the one or more polyvinyl alcohol polymers with the one or more phenylboronate-containing copolymers.

11. The method of claim 10, wherein dissolving the one or more polyvinyl alcohol polymers prior to mixing the one or more polyvinyl alcohol polymers with the one or more phenylboronate-containing copolymers occurs at a temperature of at least 70° C.

12. The method of claim 11, further comprising allowing the one or more polyvinyl alcohol polymers to cool to at least 40° C. after dissolving the one or more polyvinyl alcohol polymers and prior to mixing the one or more polyvinyl alcohol polymers with the one or more phenylboronate-containing copolymers.

13. The method of any of claim 8, wherein mixing the one or more polyvinyl alcohol polymers with the one or more phenylboronate-containing copolymers to form the mixture occurs at a pH from 5 to 9.

14. A method for tissue engineering comprising:
   culturing cells on the hydrogel scaffold of claim 1 to form one or more cell-layers, wherein the scaffold is configured for cell growth into one or more of cell-sheets or tissues;
   dissolving the hydrogel scaffold with a saccharide solution; and
   harvesting the one or more cell-layers.

15. The method of claim 14, wherein the hydrogel scaffold includes one or more polyvinyl alcohol polymers.

16. The method of claim 14, wherein the one or more phenylboronate-containing copolymers includes one or more phenylboronate ligands, one or more acrylic monomers, and one or more alkaline tertiary amines.

17. The method of claim 16, wherein the one or more phenylboronate ligands are selected from the group consisting of 4-vinylphenylboronic acid, N-acryloyl-3-aminophenylboronic acid, 3-(2-carboxyvinyl)phenylboronic acid, 4-(1,6-dioxo-2,5-diaza-7-oxamyl)phenylboronic acid, and [2-(diethylamino)carbonyl-4-bromomethyl]phenylboronate, or any combination thereof.

18. The method of claim 16, wherein the one or more acrylic monomers are selected from the group consisting of acrylamide; N-isopropylacrylamide; N,N-dimethylacrylamide; 2-hydroxyethylmethacrylate; N-Hydroxyethyl acrylamide; methacrylamide; methacrylic acid; acrylic acid; N-vinyl-2-pyrrolidone; 4-pentenoic acid; N-isopropylmethacrylamide; N-methoxymethyl-N-isopropylacrylamide; and 2-(dimethylmaleimido)-N-ethylacrylamide, or any combination thereof.

19. The method of claim 16, wherein the one or more alkaline tertiary amines are selected from the group consisting of N,N-dimethylaminoethylmethacrylate; N,N-dimethylaminopropylacrylamide; N,N-diethylaminoethyl methacrylate; and 2-(N,N-Dimethylamino)ethyl methacrylate, or any combination thereof.

20. The method of claim 14, wherein culturing the cells on the hydrogel scaffold occurs at a pH from 5 to 9.

* * * * *

UNITED STATES PATENT AND TRADEMARK OFFICE
CERTIFICATE OF CORRECTION

| | |
|---|---|
| PATENT NO. | : 8,883,503 B2 |
| APPLICATION NO. | : 13/885839 |
| DATED | : November 11, 2014 |
| INVENTOR(S) | : Kumar |

Page 1 of 1

It is certified that error appears in the above-identified patent and that said Letters Patent is hereby corrected as shown below:

On the Title Page

On Page 2, in Item (56), under "OTHER PUBLICATIONS", in Column 1, Line 22, delete "bFGF in" and insert -- bFGF on --, therefor.

On Page 2, in Item (56), under "OTHER PUBLICATIONS", in Column 2, Line 3, delete "Croasslinking" and insert -- Crosslinking --, therefor.

In the Specification

In Column 1, Line 7, delete "application of" and insert -- application filing under 35 U.S.C. §371 of --, therefor.

In Column 7, Line 39, delete "a ECM" and insert -- an ECM --, therefor.

In Column 9, Line 61, delete "p-(waminoethyl)phenylboronate," and insert -- p-(aminoethyl)phenylboronate, --, therefor.

In Column 13, Line 18, delete "a illustrative" and insert -- an illustrative --, therefor.

In Column 17, Line 57, delete "a AVD-PVA" and insert -- an AVD-PVA --, therefor.

In the Claims

In Column 20, Line 14, in Claim 13, delete "of any of claim" and insert -- of claim --, therefor.

Signed and Sealed this
First Day of September, 2015

Michelle K. Lee
*Director of the United States Patent and Trademark Office*